United States Patent [19]

Hartman et al.

[11] Patent Number: 5,362,412
[45] Date of Patent: Nov. 8, 1994

[54] BIODEGRADABLE BLEACH STABILIZERS FOR DETERGENTS

[75] Inventors: JudithAnn R. Hartman, Columbia, Md.; Richard P. Woodbury, Amherst, N.H.

[73] Assignee: Hampshire Chemical Corp., Lexington, Mass.

[21] Appl. No.: 686,643

[22] Filed: Apr. 17, 1991

[51] Int. Cl.$^5$ ............................................. C11D 3/395
[52] U.S. Cl. ................... 252/94; 252/174.19; 252/186.25; 252/186.29; 252/186.34; 423/272
[58] Field of Search ............ 252/94, 102, 106, 174.19, 252/186.25, 186.29, 186.34, 186.36; 423/272

[56] References Cited

U.S. PATENT DOCUMENTS

| | | | |
|---|---|---|---|
| 3,683,014 | 8/1972 | Yang | 260/513 N |
| 3,697,453 | 10/1972 | Tate et al. | 252/546 |
| 4,268,424 | 5/1981 | Hall et al. | 252/546 |
| 4,412,943 | 11/1983 | Hirota et al. | 252/546 |
| 4,762,645 | 8/1988 | Tucker et al. | 252/544 |
| 4,767,558 | 8/1988 | Ouhadi et al. | 252/99 |
| 4,824,604 | 4/1989 | Yahagi et al. | 252/546 |
| 4,827,014 | 5/1989 | Baur et al. | 558/441 |
| 4,900,475 | 2/1990 | Ramachandran et al. | 252/532 |
| 4,983,315 | 1/1991 | Glogowski et al. | 252/102 |
| 4,997,587 | 3/1991 | Baur et al. | 252/102 |
| 5,112,530 | 5/1992 | Baur et al. | 252/548 |
| 5,211,927 | 5/1993 | Itani et al. | 423/272 |

FOREIGN PATENT DOCUMENTS

| | | |
|---|---|---|
| 0137475 | 4/1985 | European Pat. Off. ............ 252/544 |
| 287885 | 4/1988 | European Pat. Off. . |
| 356972A2 | 3/1990 | European Pat. Off. . |
| 3739610 | 6/1989 | Germany . |
| 63-235947 | 9/1988 | Japan . |
| 1306331 | 2/1973 | United Kingdom . |
| 592818 | 2/1978 | U.S.S.R. . |

OTHER PUBLICATIONS

V. M. Nikol'skii et al., "Russian Journal of Inorganic Chemistry", 20(12) pp. 1764–1765 (1975).
Ch. Gousetis et al., Tenside Surf. Det., 27, pp. 41–45 (1990). (translation included).
N. K. Dzyuba et al., Russian Journal of Inorganic Chemistry, 24(4), pp. 542–544 (1979).
F. B. Zienty et al., Journal of Organic Chemistry, 31, pp. 4240–4244 (1966).
V. M. Nikol'skii et al., Russian Journal of Chemistry, 21(3), pp. 461–462 (1976).
I. P. Gorelov et al., translated from Zhurnal Obshchei Khimii, 48(11), pp. 2596–2600 (1978).

*Primary Examiner*—Gary P. Straub
*Assistant Examiner*—Timothy C. Vanoy
*Attorney, Agent, or Firm*—Nields & Lemack

[57] ABSTRACT

A process of stabilizing bleaching agents in a detergent composition using a nonphosphorus-containing biodegradable stabilizer. The process involves incorporating into a detergent composition containing a bleaching agent, a biodegradable compound of the formula

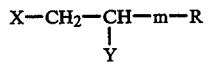

in which m is NR' or sulfur; X is SO$_3$H or COOH; Y is hydrogen, SO$_3$H or COOH; R and R' are, independently, hydrogen, —CH(Z)CH$_2$(Z'), —CH(Z)CH(-Z')(Z") or —CH$_2$COOH; and Z, Z' and Z" are, independently, hydrogen, OH, SO$_3$H or COOH; or a sodium, potassium or ammonium salt thereof, in an amount sufficient to stabilize the bleaching agent. Novel detergent compositions containing the biodegradable bleach stabilizers are also disclosed.

17 Claims, No Drawings

BIODEGRADABLE BLEACH STABILIZERS FOR DETERGENTS

FIELD OF THE INVENTION

The present invention relates to stabilizers for bleaching agents and to detergent compositions containing the same.

BACKGROUND OF THE INVENTION

Bleaching agents have long been used in laundry detergents to enhance the overall cleaning action thereof. Instability of bleaching agents in detergents is mediated principally by metal ion contamination in the detergent themselves, in the wash liquors and in the textiles and fabrics being cleaned. For example, the hydrogen peroxide responsible for the bleaching action in detergent formulas containing a peroxide-based bleaching agent, acts by dissociating into perhydroxyl ion:

$$H_2O_2 \rightarrow HOO^- + H^+$$

This ion attacks the conjugated double bonds which make up most color causing organics or stains. If metal ions (e.g., $Cu^{II}$, $Fe^{III}$, $Mn^{II}$) are present the perhydroxyl ion reacts instead with the hydrogen peroxide causing both species to degrade before they can remove stains. As a result, bleach containing laundry detergents have heretofore been made more efficient by the addition of complexing agents which tie up transition metal ions thus reducing the destructive degradation of the bleaching component.

Examples of conventional acknowledged complexing agents heretofore used in detergents include nitrilotriacetic acid (NTA), ethylenediaminetetraacetic acid (EDTA), ethylenediaminetetramethylenephosphonic acid (EDTMP), propylenediaminetetraacetic acid (PDTA), hydroxypropylenediaminetetraacetic acid (HPDTA), hydroxyethanediphosphonic acid, diethylenetriaminetetraacetic acid, diethylenetriaminetetramethylenephosphonic acid, hydroxyethylimino, diacetic acid, hydroxyethylethylenediaminetriacetic acid diethylenetriaminepentaacetic acid and also for example diethanolglycine, ethanolglycine, citric acid, glucoheptonic acid or tartaric acid, as found for example under the heading of Waschmittel in Ullmann's Encyklopädie der technischen Chemie, 4th edition, volume 24, pages 63-160, in particular pages 91-96, Verlag Chemie, Weinheim, 1983.

The action of the existing complexing agents, some of which are used on a large scale, is not always optimal to stabilize bleaching agents in detergent compositions. For instance, NTA makes a very good complexing agent and, in detergents, a fairly good builder for improving the whitening effect and for preventing deposits which cause incrustations and graying on the fabric. However, its performance as a bleach stabilizer is comparatively poor. Even EDTA, despite its good complexing action toward heavy metals, is only a moderate bleach stabilizer in detergents.

In most cases, the biodegradability of prior art complexing agents also leaves something to be desired. For instance, EDTA turns out to be insufficiently biodegradable in conventional tests, as do PDTA, HPDTA and certain phosphonates which, furthermore, are frequently undesirable on account of their phosphorus content.

It is an object of the present invention to provide efficacious bleach stabilizers for detergents which have good complexing properties, is ecologically safe, ideally contains no phosphorus and is readily biodegradable.

It is a related object of the invention to provide a method of stabilizing bleaching agents in detergent formulations by incorporating into said detergent formulations an effective bleach stabilizing amount of a biodegradable nonphosphorus-containing bleach stabilizer.

Further, it is an object of the invention to provide improved detergent formulations containing the biodegradable nonphosphorus-containing bleach stabilizers of the invention.

Other important objects of this invention will become apparent from the ensuing description and appended claims.

SUMMARY OF THE INVENTION

We have found that the aforegoing objects are achieved by employing as a bleach stabilizer in detergent formulations, an effective bleach stabilizing amount of a compound of the formula:

$$X-CH_2-CH-m-R \qquad \text{Formula I}$$
$$|$$
$$Y$$

in which m is NR' or sulfur;
X is $SO_3H$ or COOH;
Y is hydrogen, $SO_3H$ or COOH;
R and R' are independently, hydrogen, $-CH(Z)CH_2(Z')$, $-CH(Z)CH(Z')(Z'')$ or $-CH_2COOH$; and
Z, Z' and Z'' are, independently, hydrogen, OH, $SO_3H$ or a COOH radical; and wherein any COOH or $SO_3H$ radical may be present in the form of its sodium, potassium, ammonium or substituted ammonium salt.

The term "substituted ammonium" as used herein and in the appended claims refers to an ammonium radical substituted with one or more alkyl groups having from 1 to 4 carbon atoms.

The present invention provides as preferred stabilizers, compounds of Formula I in which X and Y are both COOH or the sodium, potassium, or ammonium or substituted ammonium salt thereof; and Z, Z' and Z'' are, independently, hydrogen or —COOH or a sodium, potassium, ammonium or substituted ammonium salt thereof.

Specific examples of stabilizers in accordance with the invention include, for example, cysteic-N, N-diacetic acid; cysteic acid-N-monoacetic acid; alanine-N-monoacetic acid; N(3-hydroxysuccinyl) aspartic acid; and N-[2-(3-hydroxysuccinyl)]-L-serine. Exemplary of the most preferred stabilizers are β-alanine-N,N-diacetic acid; aspartic acid-N,N-diacetic acid; iminodisuccinic acid; and aspartic acid-N-monoacetic acid; or their alkali metal or ammonium salts.

The compounds of Formula I may be readily prepared by the use of steps generally described in the literature or by methods analogous or similar thereto and within the skill of the art.

The bleach stabilizers of the invention may be prepared by reacting an alkali metal salt of an appropriately substituted amino carboxylic acid with an alkali metal salt of an appropriately substituted reference, to yield the corresponding appropriately substituted organic acid salt. Treatment of the organic salt with a mineral acid (e.g., HCl) or an acidic ion-exchange resin liberates the free acid to afford a compound of Formula I.

The compounds of Formula I can also be prepared by reacting an appropriate amine with formaldehyde and either hydrogen cyanide or an alkali metal cyanide as described in U.S. Pat. Nos. 2,855,428, 3,610,628 and 2,497,645.

The compounds of Formula I may also be prepared in a manner as described in U.S. Pat. No. 4,827,014, herein incorporated by reference. In accordance with this method, the stabilizers of the invention are prepared by reacting a compound of Formula II

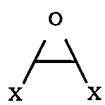 Formula II where X is a substituent within the meaning of Formula I, with an appropriately substituted amine and, if as the case may be amide, ester or nitrile groups are present, hydrolyzing these groups in the presence of and acid or base, to yield a free acid or a salt conforming to Formula I.

Where m is sulfur, compounds of Formula I may be prepared by reacting the appropriate mercaptocarboxylic acid with maleic acid in an aqueous solution under neutral, acidic or basic conditions.

Bleach stabilizers in accordance with the invention may also be prepared by method analogous to the procedure described in European Patent Application Publication No. 0,356,972 A2, herein incorporated by reference, where an appropriately substituted imino carboxylic acid or its alkali metal or ammonium salt is reacted with acrylic acid in a non-basic or an alkaline or nitrogen basic aqueous medium to yield a compound of Formula I.

Stabilizers of the invention may also be prepared in the manner as described in U.S. Pat. No. 3,929,874, herein incorporated by reference, wherein an appropriately substituted amine is reacted with epoxysuccinic acid in a basic aqueous medium to yield a compound of Formula I.

Bleaching agents which may be stabilized in accordance with the invention are, in particular, hydrogen peroxide and derivatives thereof or available chlorine compounds. Of the bleaching agent compounds which provide $H_2O_2$ in water, sodium perborate hydrates, such as $NaBO_2.H_2O_2.3H_2O$ and $NaBO_2.H_2O_2$, are of particular importance. However, it is also possible to use other $H_2O_2$-providing borates. These compounds can be replaced in part or in full by other sources of active oxygen, in particular by peroxyhydrates, such as peroxycarbonates, peroxyphosphonates, citrate perhydrates, urea-$H_2O_2$, or melamine-$H_2O_2$ compounds and also by $H_2O_2$-providing peracid salts, for example caroates, perbenzoates or peroxyphthalates.

Aside from stabilizers according to the invention, customary water-soluble and/or water-insoluble stabilizers for peroxy compounds can be incorporated together with the former in amounts from 0.25 to 10% by weight, based on the peroxy compound. Suitable water-insoluble stabilizers are the magnesium silicates MgO:-$SiO_2$ from 4:1 to 1:4, preferable from 2:1 to 1:2, in particular 1:1, in composition usually obtained by precipitation from aqueous solutions. In their place it is also possible to use other alkaline earth metals of corresponding composition.

To obtain a satisfactory bleaching action even in washing below 80° C., in particular in the range from 60° to 40° C., it is advantageous to incorporate bleach activators in the detergent, advantageously in an amount from 5 to 30% by weight, based on the $H_2O_2$ providing compound.

Activators for peroxy-compounds which provide $H_2O_2$ in water are certain N-acyl and O-acyl compounds, in particular acetyl, propionyl or benzyl compounds, which form organic peracids with $H_2O_2$ and also carbonic and pyrocarbonic esters. Useful compounds are inter alia:

N-diacylated and N,N'-tetraacylated amines, e.g. N,N,N',N'-tetraacetyl-methylenediamine or -ethylenediamine, N,N-diacetylaniline and N,N-diacetyl-p-toluidine, and 1,3-diacylated hydantoins, alkyl-N-sulfonylcarboxamides, N-acylated cyclic hydrazides, acylated triazoles or urazoles, e.g. monoacetylmaleohydrazide, O,N,N-trisubstituted hydroxylamines, e.g. O-benzoyl-N,N-succinylhydroxylamine, O-acetyl-N,N-succinylhydroxylamine, O-p-methoxybenzoyl-N,N-succinylhydroxylamine, O-p-nitrobenzoyl-N,N-succinylhydroxylamine and O,N,N-triacetylhydroxylamine, carboxylic anhydrides, e.g. benzoic anhydride, m-chlorobenzoic anhydride, phthalic anhydride and 4-chlorophthalic anhydride, sugar esters, e.g. glucose pentaacetate, imidazolidine derivatives, such as 1,3-diformyl-4,5-diacetoxyimidazolidine, 1,3-diacetyl-4,5-diacetoxyimidazoline and 1,3-diacetyl-4,5-dipropionyloxyimidazolidine, acylated glycolurils, e.g. tetrapropionylglycoluril or diacetyldibenzoylglycoluril, dialkylated 2,5-diketopiperazines, e.g. 1,4-diacetyl-2,5-diketopiperzine, 1,4-dipropionyl-2,5-diketopiperzine, and 1,4-dipropionyl-3,6-dimethyl-2,5-diketopiperazine, acetylation and benzoylation products of propylenediurea or 2,2-dimethylpropylenediurea, the sodium salt of p-(ethoxycarbonyloxy)benzoic acid and of p-(propoxycarbonyloxy) benzenesulfonic acid and also the sodium salts of alkylated or acylated phenolsulfonic esters, such as p-acetoxybenzenesulfonic acid, 2-acetoxy-5-nonylbenzenesulfonic acid, 2-acetoxy-5-propylbenzenesulfonic acid or of isononanoyloxyphenylsulfonic acid.

The bleaching agents used can also be active chlorine compounds of the inorganic or organic type. Inorganic active chlorine compounds include alkali metal hypochlorites which can be used in particular in the form of their mixed salts and adducts on orthophosphates or condensed phosphates, for example on pyrophosphates and polyphosphates or on alkali metal silicates. If the detergent contains monopersulfates and chlorides, active chlorine will form in aqueous solution.

Organic active chlorine compounds are in particular the N-chlorine compounds where one or two chlorine atoms are bonded to a nitrogen atom and where preferably the third valence of the nitrogen atom leads to a negative group, in particular to a CO or $SO_2$ group. These compounds include dichlorocyanuric and trichlorocyanuric acid and their salts, chlorinated alkylguanides or alkylbiguanides, chlorinated hydantoins and chlorinated melamines.

Bleaching stabilizers of the invention may be used in detergent formulations in general in an amount from about 0.01 to 10% by weight, preferably from 0.05 to 6% by weight, most preferably 0.1 to 2.0% by weight, based on the total weight of the detergent formulations.

The stabilizers according to the invention can also be used in detergent formulations together with other prior art constituents e.g. complexing agents, builders, co-builders, surfactants, whiteners, etc., in which case the general properties can be substantially improved in respect of sequestration, incrustation inhibition, grayness inhibition, primary washing action and bleaching action.

Detergent formulations which, based on the total weight, contain from 0.01 to 10%, preferably from 0.05 to 6.0%, by weight of a compound in accordance with the invention generally contain as additional constituents, based on the total weight, from 6 to 25% by weight of surfactants, from 15 to 50% by weight of builders with or without cobuilders, from 5 to 35%, typically 15 to 20%, by weight of bleaching agents, with or without bleaching agent activators, and from 3 to 30% by weight of assistants, such as enzymes, foam regulants, corrosion inhibitors, optical brighteners, scents, dyes or formulation aids, e.g. sodium sulfate.

Customary constituents of detergent formulations referred to above in general terms are recited in terms of examples below:

Suitable surfactants are those which contain in the molecule one or more hydrophobic organic radicals and one or more water-solubilizing anionic, zwitterionic or nonionic groups. The hydrophobic radicals usually are aliphatic hydrocarbyl of 8 to 26, preferably 10 to 22, in particular 12 to 18, carbon atoms or aromatic alkyl having 6 to 18, preferably 8 to 16, aliphatic carbon atoms.

Suitable synthetic anionic surfactants are in particular those of the sulfonate, sulfate or synthetic carboxylate type.

Suitable surfactants of the sulfonate type are alkylbenzenesulfonates having 4 to 15 carbon atoms in the alkyl moiety, mixtures of alkene and hydroxyalkanesulfonates and also disulfonates as obtained for example from monoolefins having a terminal or nonterminal double bond by sulfonation with gaseous sulfur trioxide and subsequent alkaline or acid hydrolysis of the sulfonation products. Also suitable are alkanesulfonates obtainable from alkanes by sulfochlorination or sulfoxidation and subsequent hydrolysis or neutralization or by bisulfite addition onto olefins. Further useful surfactants of the sulfonate type are the esters of alpha-sulfo fatty acids, for example the alpha-sulfonic acids of hydrogenated methyl or ethyl esters of coconut, palm kernel or tallow fat acid.

Suitable surfactants of the sulfate type are the sulfuric monoesters of primary alcohols, for example coconut fat alcohols, tallow fat alcohols or oleyl alcohol, and those of secondary alcohols. Also suitable are sulfated fatty acid alkanolamines, fatty acid monoglycerides or reaction products of from 1 to 4 moles of ethylene oxide with primary or secondary fatty alcohols or alkylphenols.

Further suitable anionic surfactants are the fatty acid esters or fatty amides of hydroxy- or aminocarboxylic or sulfonic acids, for example the fatty acid sarcosides, glycolates, lactates, taurides or isothionates.

Anionic surfactants can be present in the form of their sodium, potassium and ammonium salts and also as soluble salts of organic bases, such as mono-, di-, or triethanolamine. Also possible are ordinary soaps, i.e. salts of natural fatty acids.

Suitable nonionic surfactants (nonionics) are for example adducts of from 3 to 40, preferably 4 to 20, moles of ethylene oxide on 1 mole of fatty alcohol, alkylphenol, fatty acid, fatty amine, fatty acid amide or alkanesulfonamide. Of particular importance are the adducts of from 5 to 16 moles of ethylene oxide on coconut or tallow fat alcohols, on oleyl alcohol or on synthetic alcohols of 8 to 18, preferably 12 to 18, carbon atoms, and also on mono- or dialkylphenols of 6 to 14 carbon atoms in the alkyl(s). Besides these water-soluble nonionics, however, it is also possible to use water-insoluble or incompletely water-soluble polyglycol ethers having 1 to 4 ethylene glycol ether radicals in the molecule, in particular if used together with water-soluble nonionic or anionic surfactants.

Further suitable nonionic surfactants are the water-soluble adducts of ethylene oxide on propylene glycol ether, alkylenediaminopolypropylene glycol and alkylpolypropylene glycol having 1 to 10 carbon atoms in the alkyl chain which contain from 20 to 250 ethylene glycol ether groups and from 10 to 100 propylene glycol ether groups and where the polypropylene glycol ether chain acts as a hydrophobic radical.

It is also possible to use nonionic surfactants of the amine oxide or sulfoxide type.

The foaming power of surfactants can be enhanced or reduced by combining suitable types of surfactants. A reduction can also be obtained by adding nonsurfactant like organic substances.

Suitable builder substances are for example: wash alkalis, such as sodium carbonate and sodium silicate, or complexing agents, such as phosphates, or ion exchangers, such as zeolites, and mixtures thereof. These builder substances have as their function to eliminate the hardness ions, which come partly from the water, partly from dirt or the textile material, and to support the surfactant action. Aside from the abovementioned builder substances, the builder component may further contain cobuilders. In modern detergents, it is the function of cobuilders to undertake some of the functions of phosphates, e.g. sequestration, soil antiredeposition and primary and secondary washing action.

The builder components may contain for example water-insoluble silicates as described for example in German Laid-Open Application DE-OS No. 2,412,837 and/or phosphates. As a phosphate it is possible to use pyrophosphate, triphosphate, higher polyphosphates and metaphosphates. Similarly, phosphorus-containing organic complexing agents, such as alkanepolyphosphonic acids, amino- and hydroxy-alkanepolyphosphonic acids and phosphonocarboxylic acids, are suitable for use as further detergent ingredients. Examples of such detergent additives are the following compounds: methanediphosphonic acid, propane-1,2,3-triphosphonic acid, butane-1,2,3,4-tetraphosphonic acid, polyvinylphosphonic acid, 1-aminoethane-1,1-diphosphonic acid, 1-amino-1-phenyl-1,1-diphosphonic acid, aminotrismethylenetriphosphonic acid, methylamino- or ethylamino-bismethylenediphosphonic acid, ethylenediaminetetramethylenetetraphosphonic acid, diethylenetriaminopentamethylenepentaphosphonic acid, 1-hydroxyethane-1,1-diphosphonic acid, phosphonoacetic and phosphonopropionic acid, copolymers of vinylphosphonic acid and acrylic and/or maleic acid and also partially or completely neutralized salts thereof.

Further organic compounds which act as complexing agents for calcium and may be present in detergent formulations are polycarboxylic acids, hydroxycarboxylic acids and aminocarboxylic acids which are usually used in the form of their water-soluble salts.

Examples of polycarboxylic acids are dicarboxylic acids of the general formula $HOOC-(CH_2)_m-COOH$ where m is 0-8, and also maleic acid, methylenemalonic acid, citraconic acid, mesaconic acid, itaconic acid, noncyclic polycarboxylic acids having 3 or more carboxyl groups in the molecule, e.g. tricarballylic acid, aconitic acid, ethylenetetracarboxylic acid, 1,1,3-propanetetracarboxylic acid, 1,1,3,3,5,5-pentanehexacarboxylic acid, hexanehexacarboxylic acid, cyclic di- or polycarboxylic acids, e.g. cyclopentanetetracarboxylic acid, cyclohexanehexacarboxylic acid, tetrahydrofurantetracarboxylic acid, phthalic acid, terephthalic acid, benzene-tricarboxylic, -tetracarboxylic or -pentacarboxylic acid and mellitic acid.

Examples of hydroxymonocarboxylic and hydroxypolycarboxylic acids are glycollic acid, lactic acid, malic acid, tartronic acid, methyltartronic acid, gluconic acid, glyceric acid, citric acid, tartaric acid and salicylic acid.

Examples of aminocarboxylic acids are glycine, glycylglycine, alanine, asparagine, glutamic acid, aminobenzoic acid, iminodiacetic acid, iminotriacetic acid, hydroxyethyliminodiacetic acid, ethylenediaminotetraacetic acid, hydroxyethylethylenediaminetriacetic acid, diethylenetriaminepentaacetic acid and higher homologues which are preparable by polymerization of an N-aziridylcarboxylic acid derivative, for example of acetic acid, succinic acid or tricarballylic acid, and subsequent hydrolysis, or by condensation of polyamines having a molecular weight of from 500 to 10,000 with salts of chloroacetic or bromoacetic acid.

Preferred cobuilder substances are polymeric carboxylic acids. These polymeric carboxylic acids shall include the carboxymethyl ethers of sugars, of starch and of cellulose.

Particularly important polymeric carboxylic acids are for example the polymers of acrylic acid, maleic acid, itaconic acid, mesaconic acid, aconitic acid, methylenemalonic acid, citraconic acid and the like, the copolymers between the aforementioned carboxylic acids, for example a copolymer of acrylic acid and maleic acid in a ratio of 70:30 and having a molecular weight of 70,000, or copolymers thereof with ethylenically unsaturated compounds, such as ethylene, propylene, isobutylene, vinyl alcohol, vinyl methyl ether, furan, acrolein, vinyl acetate, acrylamide, acrylonitrile, methacrylic acid, crotonic acid and the like, e.g. the 1:1 copolymers of maleic anhydride and methyl vinyl ether having a molecular weight of 70,000 or the copolymers of maleic anhydride and ethylene and/or propylene and/or furan.

The cobuilders may further contain soil antiredeposition agents which keep the dirt detached from the fiber in suspension in the liquor and thus inhibit graying. Suitable for this purpose are water-soluble colloids usually of an organic nature, for example the water-soluble salts of polymeric carboxylic acids, glue, gelatin, salts of ethercarboxylic acids or ethersulfonic acids of starch and of cellulose or salts of acid sulfates of cellulose and of starch. Even water-soluble polyamides containing acid groups are suitable for this purpose. It is also possible to use soluble starch products and starch products other than those mentioned above, for example degraded starch, aldehyde starches and the like. Polyvinylpyrrolidone is also usable.

Examples of additional assistants are: Suitable foam regulants, in particular if surfactants of the sulfonate or sulfate type are used, are surface-active carboxybetaines of sulfobetaines and also the abovementioned nonionics of the alkylolamide type. Also suitable for this purpose are fatty alcohols or higher terminal diols.

Reduced foaming, which is desirable in particular for machine washing, is frequently obtained by combining various types of surfactants, for example sulfates and/or sulfonates, with nonionics and/or with soaps. In the case of soaps, the foam inhibition increases with the degree of saturation and the number of carbon atoms of the fatty acid ester; soaps of saturated $C_{20}-C_{24}$-fatty acids, therefore, are particularly suitable for use as foam inhibitors.

The nonsurfactant-like foam inhibitors include possibly chlorine-containing N-alkylated aminotrizines which are obtained by reacting 1 mole of cyanuric chloride with from 2 to 3 moles of a mono-and/or dialkylamine having 6 to 20, preferably 8 to 18, carbon atoms in the alkyl. A similar effect is possessed by propoxylated and/or butoxylated aminotriazines, for example products obtained by addition of from 5 to 10 moles of propylene oxide onto 1 mole of melamine and further addition of from 10 to 50 moles of butylene oxide onto this propylene oxide derivative.

Other suitable nonsurfactant-like foam inhibitors are water-insouble organic compounds, such as paraffins or haloparaffins having melting points below 100° C., aliphatic $C_{18}$- to $C_{40}$-ketones and also aliphatic carboxylic esters which, in the acid or in the alcohol moiety, possibly even both these moieties, contain not less than 18 carbon atoms (for example triglycerides or fatty acid fatty alcohol esters); they can be used in particular in combinations of surfactants of the sulfate and/or sulfonate type with soaps for foam inhibition.

The detergents may contain optical brighteners for cotton, for polyamide, for polyacrylonitrile of for polyester fabrics. Examples of suitable optical brighteners are derivatives of diaminostilbenedisulfonic acid for cotton, derivatives of 1,3-diarylpyrazolines for polyamide, quaternary salts of 7-methoxy-2-benzimidazol-2'-ylbenzofuran or of derivatives from the class of the 7-[1',2',5'-triazol-1'yl]-3-[1''',2''',4'''-triazol-1''yl]coumarins for polyacrylonitrile. Examples of brighteners suitable for polyester are products of the class of the substituted styryls, ethylenes, thiophenes, naphthalenedicarboxylic acids or derivatives thereof, stilbenes, coumarins and naphthalimides.

Further possible assistants or formulation aids are the conventional substances known to those skilled in the art, for example solubilizers, such as xylenesulfonates or cumenesulfonates, standardizing agents, such as sodium sulfate, enzymes or scent oils.

It will be apparent from the foregoing that the compositions of this invention may be formulated according to any of the various commercially desirable forms. For example, the formulations of this invention may be provided in granular form, in liquid form, in tablet form, or in the form of flakes or powders.

The relative proportions and absolute quantities of the several ingredients of the finished compositions of this invention are susceptible to variation and in most cases will vary depending upon such factors as the nature of the particular ingredients being utilized, the end use of which the composition is intended to be put, the relative costs of the ingredients, and the like. The preferred compositions of this invention are phosphorus-free although it may be desired to include therein reduced quantities of conventional phosphorus-containing materials such as sodium tripolyphosphate, tetrasodium pyrophosphate, salts of substituted methylene disphosphonic acids, long chain tertiary phosphine oxides, or the like.

The invention is not to be limited to any particular method of mixing the stabilizer and the detergent. The stabilizer may be mechanically mixed in, crutched in the detergent in the form of a slurry, or dissolved in a solution of the detergent. In addition, the stabilizer may be admixed with the detergent in any of the forms in which the detergent is manufactured, as well as being added simultaneously or separately to an aqueous solution. In any event, the stabilizers of the invention are intended to be used with the detergent at the time of application as a cleansing agent.

In order to further illustrate the invention detailed hereinabove, the following examples are presented.

EXAMPLE I (Preparation of Aspartic acid-N,N-diacetic acid, tetrasodium salt)

A solution of 5.32 g (40 mmol) of aspartic acid and 3.2 g (80 mmol) of sodium hydroxide in 50 ml of water was heated to 60° C. with stirring. A solution of 12.81 g (110 mmol) of sodium chloroacetate in 20 ml water was added dropwise over 12 hrs. During this addition, the pH of the reactor solution was maintained in the range 9-10 by addition of 10% sodium hydroxide solution until a total of 4.4 g (110 mmol) sodium hydroxide had been added. The reaction was heated at 60° C. for an additional 12 hours. The solution was adjusted to a pH of 3 with concentrated hydrochloric acid and was cooled to 5° C. A threefold volume of methanol was added and the resulting precipitate was filtered off and washed with cold methanol.

EXAMPLE II (Preparation of Aspartic acid-N-monoacetic acid)

A solution of 69.63 g (600 mmol) of maleic acid, 68 g (1700 mmol) of sodium hydroxide, and 37.53 (500 mol) of glycine in 200 ml water was heated at reflux for 17 hours. The resulting solution was cooled to room temperature and the pH was adjusted to 3 with concentrated hydrochloric acid. The precipitated mixture of maleic and fumeric acid was removed by filtration and the resulting solution was concentrated to dryness to yield the product as a white solid.

EXAMPLE III (Preparation of N-(3-hydroxy succinyl) aspartic acid)

A solution of 5.72 g (43 mmol) of aspartic acid in 100 ml of water was neutralized with 3.44 g (86 mmol) of sodium hydroxide. To this was added 7.57 (43 mmol) of epoxysuccinic acid. The resulting solution was refluxed overnight. The resulting solution was cooled and was concentrated under reduced pressure to get a crude product as a light yellow solid. Repeated crystallization from water (pH=10)/methanol yielded the pure product as a white solid.

EXAMPLE IV (Preparation of Iminodisuccinic acid)

A mixture of 12.77 g (110 mmol) maleic acid, 19.2 g (300 mmol) of 28% aqueous ammonia, and 13.3 g (100 mmol) aspartic acid in 75 ml water was heated to 95° C. with stirring. The solution was adjusted to a pH of 9 with 10% aqueous sodium hydroxide, then stored at 95° C. for 20 hours. The resulting clear solution was cooled to room temperature and 11.95 g (300 mmol) concentrated hydrochloric acid was added. The resulting precipitate of maleic and fumeric acid was removed by filtration, and the supernatant was concentrated under pressure to yield the product as a white solid.

EXAMPLE V (Preparation of Carboxymethylmercaptosuccinic acid)

A solution of 180 g (10 mol) of water and 98 g (1.0 mol) of maleic anhydride was heated to 40° C. To this solution was added 92 g (1.0 mol) of thioglycolic acid and the reaction mixture was heated to 90° C. with stirring. After three (3) hours at 90° C., the water was evaporated off under reduced pressure. The resulting molten product was cast and ground prior to use.

EXAMPLE VI (Perborate Stabilization in the Presence of Metal Ions)

The hydrogen peroxide responsible for the bleaching action in sodium perborate based laundry detergents is decomposed catalytically by transition metal ions such as $Mn^{II}$ and $Cu^{II}$. This degradation can be prevented by complexing the metal ions.

The peroxide stabilizing effect of stabilizers in accordance with the invention was tested by measuring the peroxide present before and after storage in a hot aqueous solution which contains copper or manganese ions.

Procedure

A solution of 0.2 g ($2 \times 10^{-3}$ mols) sodium perborate monohydrate; 10.0 ml of hardness standard (3:1 $CaCl_2:MgCl_2$, $1 \times 10^{-6}$ mols total); 3.0 ml of metal standard ($5.4 \times 10^{-8}$ mol $Mn^{II}$ or $4.7 \times 10^{-8}$ mols $Cu^{II}$); and 2.0 ml stabilizer solution ($4.2 \times 10^{-7}$ mols stabilizer) was diluted to 100 ml with distilled water. The pH was adjusted to 10.1 and the solution was stirred at 70° C. for 20 minutes. Ten ml aliquots of the solution were tested after 10 minutes by first neutralizing the solution with sulfuric acid and then titrating with iodine and starch.

The percentage of peroxide remaining after storage was determined using a starch/iodine titration procedure. Results are recorded in Table I below.

TABLE I

Effect of Bleach Stabilizers to Stabilize Perborate in the Presence of $Mn^{+2}$ and $Cu^{+2}$ Ions

| Stabilizer | Stability in Presence of $Mn^2$ Ions % Remaining | Stability in Presence of $Cu^{+2}$ Ions % Remaining |
|---|---|---|
| CMMS[1] | 54.5 | 31.3 |
| BADA[2] | 45.0 | 50.4 |
| AspDA[3] | 25.6 | 28.6 |
| ISA[4] | 13.6 | 79.0 |
| AspMA[5] | 21.5 | 0.0 |
| EDTA[6] | 87.5 | 82.8 |

[1]CMMS = Carboxymethylmercaptosuccinic acid
[2]BADA = β-alanine-N,N-diacetic acid
[3]AspDA = Aspartic acid-N,N-diacetic acid
[4]ISA = Iminodisuccinic acid
[5]AspMA = Aspartic acid-N-monoacetic acid
[6]EDTA = Ethylenediaminetetraacetic acid

EXAMPLE VII (Sodium Perborate Stabilization in Wash Liquors)

The efficiency of the bleaching action of a laundry detergent containing the stabilizers of the invention was measured by washing white poly-cotton fabric swatches previously stained with grape juice. The test was carried out using the following detergent formulation:

| | |
|---|---|
| Sodium Dodecyl Benzene Sulfonate | 12% |
| Nonylphenol | 4% |
| $Na_2SO_4$ | 30% |
| Sodium Carbonate | 20% |
| Zeolite | 29% |
| Na Silicate | 5% |

Procedure

Grape juice stained, poly-cotton fabric swatches purchased from Scientific Services, Oakland, N.J., were washed in a Tergitometer at 50° C. for 15 minutes in a wash solution containing sodium perborate-monohydrate 0.8 g/l; 4.0 g/l of the zeolite-based detergent as described above; 100 ppm Hardness (3:1 Ca:Mg); 2 ppm $Fe^{III}$; 1 ppm $Cu^{II}$; and 1 ppm $Mn^{II}$ (from AA standards); and $5.2 \times 10^{-5}$ mol/l stabilizer. The pH of the wash solution was 10.3. The swatches were then rinsed for 5 minutes in 25° C. water and air dried.

The efficiency of the bleaching action was determined by measuring the brightness ($\Delta E$) of the swatches and the percentage of soil removed from the swatches.

$\Delta E$ was calculated in accordance with ASTM E 308-66(81) standards, using the following formula:

$$\Delta E = \sqrt{(\Delta L)2 + (\Delta a)2 + (\Delta b)2}$$

wherein

L=Lightness 0 black, 100 white
a=Redness if +, Greenness if −, Gray is 0
b=Yellow if +, Blue if −, Gray is 0
$\Delta$ measurements are before and after washing Percent stain removal was calculated in duplicate in accordance with ASTM D3050-75 standards, using the following formula:

$$\% \text{ Soil Removed} = \frac{D \text{ after wash} - D \text{ before wash}}{D \text{ unstained fabric} - D \text{ before wash}}$$

where D=reflectance by detergent head with green filter (brightness).

The results were compared to results obtained for EDTA and are recorded in Table II below.

TABLE II

| Stabilizer | $\Delta E$ | % Stain Removal |
|---|---|---|
| CMMS[1] | 102.3 | 84.5 |
| BADA[2] | 98.0 | 83.3 |
| AspDA[3] | 93.9 | 83.7 |
| ISA[4] | 92.7 | 81.4 |
| AspMA[5] | 87.6 | 84.4 |
| EDTA[6] | 86.2 | 79.7 |

[1]CMMS = Carboxymethylmercaptosuccinic acid
[2]BADA = β-alanine-N,N-diacetic acid
[3]AspDA = Aspartic acid-N,N-diacetic acid
[4]ISA = Iminodisuccinic acid
[5]AspMA = Aspartic acid-N-monoacetic acid
[6]EDTA = Ethylenediaminetetraacetic acid It follows from the results that the chelating agents described above, in combination with sodium perborate, are effective in removing these stains.

EXAMPLE VIII (Determination of Biodegradability)

The biodegradability of bleach stabilizers described hereinabove was determined using the Sturm $CO_2$ Evolution Test (J. Amer. Oil Chem. Soc., 50, 159(1973)). The Sturm Test measures the ultimate biodegradation of soluble organic materials. The term "ultimate biodegradation" is defined herein to indicate the complete mineralization of material to $CO_2$, water, and inorganic salts. In this test, the $CO_2$ generated from the degradation of the stabilizer of the invention was trapped using a series of three barium hydroxide traps. The barium hydroxide reacted with the $CO_2$ to form barium carbonate and the amount of $CO_2$ evolved was determined by titrating the unreacted barium hydroxide with hydrochloric acid.

Procedure

The test was conducted in a two liter flask with the final volume of the test solution being one liter (Final volume equals the volume of the medium plus the volume of the test sample solution plus the volume of the inoculum). The test medium was a modified BOD (Biochemical Oxygen Demand) water which contains, per liter of distilled water, the following standard BOD reagent solutions:

| | | |
|---|---|---|
| 1.0 ml | magnesium sulfate | (2.25% w/v) |
| 1.0 ml | calcium chloride | (2.75% w/v) |
| 4.0 ml | ferric chloride | (0.025% w/v) |
| 1.0 ml | ammonium sulfate | (4.99% w/v) |
| 2.0 ml | phosphate buffer | (pH 7.2) | w/v = weight per volume

A stock solution of the test compound was prepared at a concentration of 1000 mg/l and the pH adjusted to 7.0 if the initial pH was outside of a 4.0–10.0 pH range.

The inoculum was prepared by taking unacclimated sludge and homogenizing it for two minutes, at room temperature, using a Waring Blender at medium speed. The homogenized sample was transferred to a beaker and left to settle for 15–30 minutes. The supernatant was carefully decanted and 10 ml of this solution was added to each test flask. Immediately prior to the beginning of the test, the viability of the test organisms was determined. There must be at least $1 \times 10^6$ microorganisms per milliliter before this inoculum can be used. The inoculum was used the day it was prepared.

Each test flask was charged with 980 ml of test medium and then purged for twenty-four hours using $CO_2$ free air. Following the removal of residual $CO_2$, the test flasks were connected to a series of three barium hydroxide traps each containing 100 ml of 0.024N barium hydroxide. Ten milliliters of the test sample stock solution was added to each flask followed by the addition of 10 ml of the inoculum prepared above.

The head space of each flask was aerated with $CO_2$ free air at a flow rate of 50–100 cc/min for the duration of the test. Every 2–3 days the first barium hydroxide trap (nearest to the test flask) was titrated using 0.05N standardized HCl and the amount of $CO_2$ evolved was determined. The remaining two barium hydroxide traps were moved forward to positions one and two and a new barium hydroxide trap was placed in position three. The length of the test was typically 26–30 days.

Included in each test were two blanks which were titrated along with the test samples. The amount $C_2$ found for each sample was determined using the following equation:

mg CO$_{2(sample)}$=[ml titrant$_{(sample)}$−ml titrant$_{(blank\ ave.)}$]×1.1

Each test also included a sample of glucose which was used as a control to guarantee the activity of the microorganisms.

Each stabilizer tested was degraded as described hereinabove with the exception that AspDA was degraded using acclimated microorganisms. The microorganisms were acclimated in a bench scale semicontinuous activate sludge system. The initial activated sludge was adjusted to a suspended solids level of 2500–3000 mg/l . The activated sludge was exposed to increasing levels of test material over a five day period (4, 8, 12, 16, and 20 mg/l ) and then maintained at 20 mg/l for an additional five days. The acclimated microorganisms were then treated as described above prior to the start of the Sturm test.

The results of each test are reported in Table III below. Results are recorded as a percentage of the theoretical CO$_2$ expected to evolve if there was 100% biodegradation. If the CO$_2$ production for the glucose flask did not plateau at 70% or more, the test results were discarded. The theoretical CO$_2$ for test samples was determined using a Total Organic Carbon Analyzer or other suitable analytical methods for determining total organic carbon.

TABLE III

| Biodegradation Properties of Aspartic Acid and β-alanine Derivatives | |
|---|---|
| Stabilizer | % of Theoret. CO$_2$ |
| CMMS[1] | 85% |
| AspDA[2] | 84% |
| AspMA[3] | 78% |
| ISA[4] | 76% |
| BADA[5] | 73% |
| citric acid | 82% |
| NTA[6] | 73% |
| glycine | 59% |
| EDTA[7] | 0% |

[1]CMMS = Carboxymethylmercaptosuccinic acid
[2]AspDA = Aspartic acid-N,N-diacetic acid
[3]AspMA = Aspartic acid-N-monoacetic acid
[4]ISA = Iminodisuccinic acid
[5]BADA = β-alanine-N,N-diacetic acid
[6]NTA = Nitrilotriacetic acid
[7]EDTA = Ethylenediaminetetraacetic acid The principles, preferred embodiments and modes of operation of the present invention have been described in the foregoing specification. The invention which is intended to be protected herein, however is not to be construed as limited to the particular forms disclosed, since these are to be regarded as illustrative rather than restrictive. Variations and changes may be made by those skilled in the art without departing from the spirit of the invention.

We claim:

1. A process of stabilizing bleaching agents in a detergent composition for textiles and fabrics, said process comprising incorporating into a detergent composition having a bleaching agent incorporated therein, a biodegradable compound of the formula.

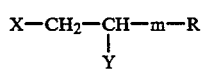

in which
m is NR' or sulfur;
X is SO$_3$H or COOH;
Y is hydrogen, SO$_3$H or COOH;
R and R' are, independently, hydrogen, —CH(Z)CH$_2$(Z'), —CH(Z)CH(Z')(Z") or —CH$_2$COOH; and
Z, Z' and Z" are, independently, hydrogen, OH, SO$_3$H or a COOH radical; except when m is —NR', X is —COOH, Y is hydrogen and R is —CH$_2$COOH, R' is not —CH$_2$COOH; or a sodium, potassium, ammonium or substituted ammonium salt thereof, in an amount sufficient to stabilize the bleaching agent, wherein the bleaching agent is selected from hydrogen peroxide and derivatives thereof which provide hydrogen peroxide is water; peroxyhydrates; and inorganic or organic active chlorine compounds.

2. The process of claim 1 in which X and Y are COOH or a sodium, potassium, or ammonium salt thereof; and Z, Z' and Z" are, independently, hydrogen or a COOH radical or a sodium, potassium, ammonium or substituted ammonium salt thereof.

3. The process of claim 1 in which the biodegradable compound is incorporated into the detergent composition in an amount of about 0.01 to 10% by weight based on the total weight of the detergent composition.

4. The process of claim 1 in which the biodegradable compound is aspartic acid-N,N-diacetic acid or a potassium, sodium or ammonium salt thereof.

5. The process of claim 1 in which the biodegradable compound is iminodisuccinic acid or a potassium, sodium or ammonium salt thereof.

6. The process of claim 1 in which the biodegradable compound is an aspartic acid-N-monoacetic acid or a potassium, sodium or ammonium salt thereof.

7. The process of claim 1 in which the biodegradable compound is cysteic acid-N,N-diacetic acid.

8. The process of claim 1 in which the biodegradable compound is carboxymethylmercaptosuccinic acid.

9. The process of claim 1 in which derivatives of hydrogen peroxide which provide hydrogen in water are selected from sodium perborate hydrates, peracid salts; urea-H$_2$O$_2$ and melamine-H$_2$O$_2$.

10. The process of claim 9 in which the peracid salts are selected from caroates, perbenzoates and peroxyphthalates.

11. The process of claim 1 in which the peroxyhydrate is selected from peroxycarbonates and peroxyphosphonates.

12. A detergent composition for textiles and fabrics comprising a bleaching agent and a bleach stabilizing compound of the formula

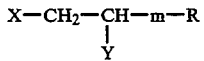

in which
m is NR' or sulfur;
X is a SO$_3$H or COOH;
Y is hydrogen, SO$_3$H or COOH;
R and R' are, independently, hydrogen, —CH(Z)CH$_2$(Z'), —CH(Z)CH(Z')(Z") or —CH$_2$COOH; and
Z, Z' and Z" are, independently, hydrogen, OH, SO$_3$H or COOH radical; except when m is —NR', X is —COOH, Y is hydrogen and R is —CH- $_2$COOH, R' is not —CH$_2$COOH; or a sodium, potassium, ammonium or substituted ammonium salt thereof, wherein said bleach stabilizing compound is present in the amount of about 0.1 to 10 percent by weight of the total weight of the detergent composition and the bleaching agent is present in the amount of about 5 to 35 percent by weight of the total weight of the detergent composition.

13. The composition of claim 12 in which the bleach stabilizing compound is present in an amount of about 0.5 to 6.0 percent by weight of the total weight of the detergent composition.

14. The composition of claim 12 in which the bleach stabilizing compound is present in an amount of about 0.1 to 2.0 percent by weight of the total weight of the detergent composition.

15. The composition of claim 12 in which the bleaching agent is present in an amount of about 15 to 20 weight of the total weight of the detergent composition.

16. The composition of claim 12 in which the biodegradable compound is aspartic acid-N,N-diacetic acid or a sodium, potassium or ammonium salt thereof.

17. The composition of claim 12 in which the biodegradable compound is an aspartic acid-N-monoacetic acid or a sodium, potassium or ammonium salt thereof.

* * * * *